US00PP09131P

United States Patent [19]

Moser

[11] Patent Number: Plant 9,131

[45] Date of Patent: May 9, 1995

[54] AZALEA PLANT NAMED CHAMPAGNE

[75] Inventor: Frank C. Moser, Alva, Fla.

[73] Assignee: Yoder Brothers, Inc., Barberton, Ohio

[21] Appl. No.: 223,723

[22] Filed: Apr. 6, 1994

[51] Int. Cl.[6] ..... A01H 5/00

[52] U.S. Cl. ..... Plt./56

[58] Field of Search ..... Plt. 55, 56, 57

[56] References Cited

PUBLICATIONS

Leach, D. G. "(Listing for) 'Champagne'", *Rhododendrons of the World,* 1961, Charles Scribner's Sons, N.Y., p. 438.

*Primary Examiner*—James R. Feyrer
*Attorney, Agent, or Firm*—Foley & Lardner

[57] ABSTRACT

An azalea plant named Champagne particularly characterized by its evergreen foliage, semi-double hose-in-hose flower with slightly frilled margins, coral-pink flower color, ease of budding, uniform plant habit and flowering response in a year round controlled program, and by its excellent cooler tolerance and keeping quality.

1 Drawing Sheet

The present invention comprises a new and distinct cultivar of Azalea, a greenhouse forcing type, hereinafter referred to as Champagne.

Champagne, identified as Code 814 during the selection process, originated from a planned cross hybridization between two selected breeding lines in a controlled breeding program in Fort Wayne, Fla. by the inventor Frank C. Moser.

The female, or seed parent of Champagne is the commercial cultivar Prize, a dark rose pink double hose-in-hose with vigorous upright habit and disclosed in U.S. Plant Pat. No. 3,795. The male, or pollen parent is a seedling known as Code 227, a proprietary breeding line.

Champagne was discovered and selected as one flowering plant within the progeny of the stated cross by the inventor Frank C. Moser in October 1988, in Fort Myers, Fla.

The first asexual reproduction of Champagne was accomplished when vegetative cuttings were taken from the initial selection in December 1988, in Fort Myers, Fla., by technicians working under formulations established and supervised by Frank C. Moser.

Horticultural examination of controlled flowerings of successive generations of plants derived from cuttings taken from the original selection has shown that the unique combination of characteristics as herein disclosed for Champagne are fixed and retained through successive generations of asexual reproduction.

Champagne has not been observed under all possible environmental conditions. The phenotype may vary significantly with variations in environment such as temperature, light intensity and day length, without, however, any variance in the genotype.

The following observations, measurements and comparisons describe plants grown in Fort Myers, Fla. in a controlled greenhouse environment and following a commercial schedule.

The following traits have been repeatedly observed and are determined to be basic characteristics of Champagne, which in combination distinguish this azalea as a new and distinct cultivar.

1. A strong coral-pink flower color (48B) upon opening, fading to a softer coral-pink color (48D) as flowers age.

2. Semi-double hose-in-hose flower with a slightly frilled petal margin. The flowers range in size from 5.5 to 8.0 cm in diameter, with 6.8 cm the average size.

3. Compact, uniform and symmetrical plant habit.

4. Rapid uniform response in year round controlled flowering programs, forcing in 30 days on average.

5. Long lasting flowers, with flowers on the plant in a simulated home environment lasting up to 21 days.

6. Very good foliage retention and no flower bud damage when cooled for 6 weeks with no lighting at 38° F.

The accompanying color photograph shows in perspective view the unique features of the new cultivar. The flower color is accurately depicted in the photograph but the foliage color, the precise color values for which are accurately noted below, is not accurately illustrated.

Of the commercial cultivars known to the inventor, the most similar in comparison to Champagne is Gloria. Champagne is similar to Gloria in that the coral-pink flower color and the flowering plant habits are somewhat alike.

Champagne differs from Gloria in that Champagne does not have a distinct flower blotch or white petal margin, and the flower from of Champagne is more double and the flower margins are frillier than those of Gloria. In groups of plants grown under the same conditions in Fort Myers, Fla., Champagne lasts up to one week longer in keeping quality trials and appears to have less plant losses to disease during the growing season than Gloria.

In the following description color references are made to The Royal Horticultural Society Color Chart. The color values were determined on Feb. 7, 1994. All readings were taken in an office under cool white fluorescent lights, facing a west window between the hours of 10:00 a.m. and 2:00 p.m.

Classification:

*Botanical.*—Rhododendron hybrida, evergreen type.

*Commercial.*—Florist forcing pot azalea.

INFLORESCENCE

A. Flower (General):

*Size.*—5.5 to 8.0 cm in diameter.

*Borne.*—Terminal cluster, usually 4 per bud, ranging from 3–5. Often more than one bud per stem.

*Form.*—Semi-double hose-in-hose. Funnel-form.

*Blooming habit.*—Once, profusely. Buds easily and uniformly in a year round flowering program. The majority of terminal buds break color within one week of the first. Flowering begins approximately thirty days after the start of forcing.

*Fragrance.*—none.

B. Corolla (Petals):

*Texture.*—Soft.

*Substance.*—Heavy.

*Shape.*—Rounded with slightly frilled margin.

*Color (fully open).*—Generally 48B, coral-pink. Upper surface: Edge: 48B. Center: 48B. Base: 48C. Lower Surface: 49A. Blotch: Between 43C and 48A.

C. Bud:

*Size.*—Medium.

*Shape.*—Conoidal.

*Color.*—48A.

*Bud sheath.*—Light green with light brown hairs.

D. Calyx:

*Form.*—Petaloid.

*Color.*—Upper surface: 48A. Lower surface: 48D.

E. Peduncle:

*Length.*—1–2 cm.

*Strength.*—Strong.

*Aspect.*—Pubescent.

F. Reproductive organs:

*Androecium (stamens).*—Number: 0 to 5. Many are fully or partially transformed into petals. Anthers: 50A. Filaments: Length: 1–2.5 cm. Color: 50C.

*Gynoecium (pistil).*—Stigma: 152D. Style: Length: 2.8–3.2 cm. Color: 48D. Ovary: Pubescent.

PLANT CHARACTERISTICS

A. Foliage:

*Type.*—Evergreen.

*Arrangement.*—Alternate.

*Shape.*—Elliptic.

*Size.*—Length: 2.5–5.0 cm. Width: 0.8–2.0 cm.

*Margin.*—Entire.

*Color.*—Immature: Upper surface: 144A. Lower surface: 146B. Mature: Upper surface: 139A. Lower surface: 146B.

*Texture.*—Leathery.

*Tomentum.*—Present on upper surface. Insignificant.

B. Stems:

*Color.*—Immature: 146D. Mature: 165B. Tomentum: 165B.

C. Plant habit: Compact, semi-upright bush which achieves a uniform, symmetrical plant is a six-inch pot when pinched three times. Total crop time to the dormant budded stage is 40–42 weeks to produce a plant approximately 30 cm in diameter and a total height of 30–36 cm. Internode lengths vary widely from 2 to 30 mm on the same stem.

D. Branching habit: Free branching, producing 3 to 4 breaks when a vegetative cutting is pinched.

E. Rooting: Roots easily in 8 to 10 weeks with 75° F. soil temperature.

F. Budding ease: Plants produce flower buds easily and uniformly year round with the use of commercially available plant growth regulators. Natural season response has not been ascertained.

H. Cooler tolerance: Plants placed in a cooler as a means of breaking dormancy perform very well. Champagne is tolerant of six weeks in an unlighted cooler without excessive bud damage or foliage loss.

I. Blooming: Plants reach the stage of 12 buds showing color in 30 days on average after the cooling treatment. This varies from 15 to 45 days depending upon time of year. Champagne flowers uniformly and profusely across the plant.

J. Shelf-life: When plants are moved to an office or home environment at the stage of eight open flowers, they maintain an attractive appearance for 21 days on average.

I claim:

1. A new and distinct cultivar of azalea named Champagne, as illustrated and described.

* * * * *

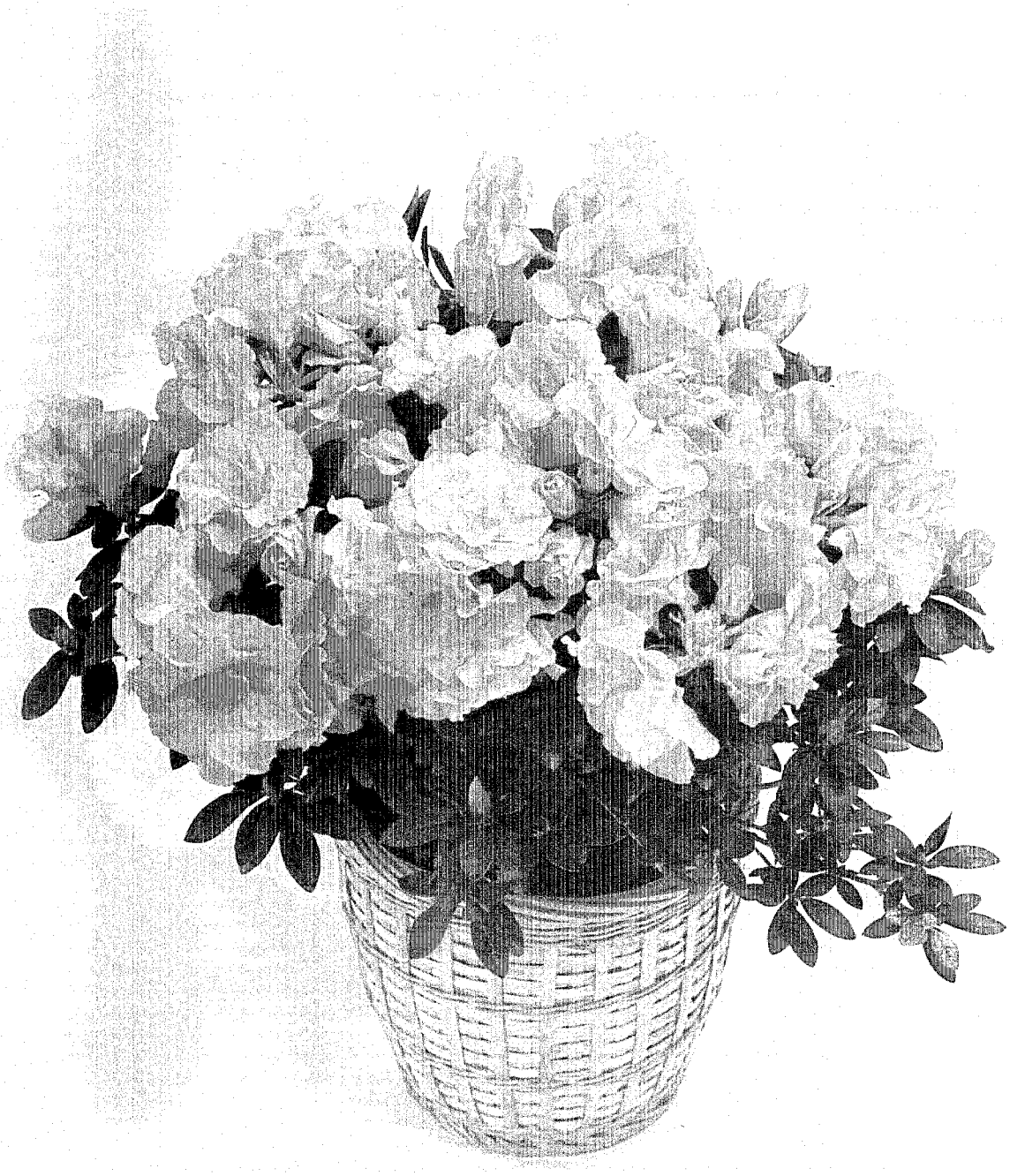

UNITED STATES PATENT AND TRADEMARK OFFICE

CERTIFICATE OF CORRECTION

PATENT NO. : PP-9,131

DATED : May 9, 1995

INVENTOR(S) : Moser

It is certified that error appears in the above-indentified patent and that said Letters Patent is hereby corrected as shown below:

Column 1, line 7, wherein "Fort Wayne," should read --Fort Myers,--

Column 2, line 25, wherein "from" should read --form--

Column 4, line 13, wherein "is" should read --in--.

Signed and Sealed this

Twenty-sixth Day of March, 1996

Bruce Lehman

*Attest:*

BRUCE LEHMAN

*Attesting Officer*

*Commissioner of Patents and Trademarks*